United States Patent [19]

Maji

[11] Patent Number: 5,635,643
[45] Date of Patent: Jun. 3, 1997

[54] IDENTIFYING SOURCE OF ACOUSTIC EMISSIONS IN STRUCTURES USING LAMB WAVES AND VIBRATION MODES

[75] Inventor: Arup K. Maji, Albuquerque, N.M.

[73] Assignee: The University of New Mexico, Albuquerque, N.M.

[21] Appl. No.: 404,708

[22] Filed: Mar. 15, 1995

[51] Int. Cl.$^6$ .................................................. G01N 29/14
[52] U.S. Cl. ................................................ 73/587; 73/786
[58] Field of Search ............................ 73/801, 587, 786, 73/579, 581, 582, 583, 594, 602; 364/506, 508, 512

[56] References Cited

U.S. PATENT DOCUMENTS

| | | | |
|---|---|---|---|
| 3,919,883 | 11/1975 | Nakamura et al. | 73/587 |
| 4,011,472 | 3/1977 | Feng | 73/587 |
| 4,092,868 | 6/1978 | Thompson et al. | 73/638 |
| 4,346,914 | 8/1982 | Livers | 280/735 |
| 4,688,429 | 8/1987 | Holroyd | 73/602 |
| 4,910,718 | 3/1990 | Horn | 367/124 |
| 5,189,914 | 3/1993 | White et al. | 73/599 |
| 5,212,988 | 5/1993 | White | 73/602 |
| 5,270,950 | 12/1993 | Cowley et al. | 364/551.01 |

OTHER PUBLICATIONS

Gong et al., "Acoustic Emission Monitoring of Steel Railroad Bridges", Materials Evaluation, pp. 883–887 (1992).

Doyle, "An Experimental Method for Determining the Location and Time of Initiation of an Unkown Dispersing Pulse", Experimental Mechanics, pp. 229–233 (1987).

Ziola et al., "Source location in that plates using cross-correlation", J. Acoust. Soc. Am., vol. 90, No. 5, pp. 2551–2556 (1991).

*Primary Examiner*—Christine K. Oda
*Attorney, Agent, or Firm*—Bruce H. Cottrell

[57] ABSTRACT

A process for global monitoring of a structure for location of a source of acoustic emissions using the vibration modes of a structure together with the repetition rate of acoustic emission events in said structure thereby allowing determination of source location of acoustic emission events in said structure is provided. Further a process for identifying the arrival of different modes of lamb waves at the same transducer distance, based on the different propagation velocities of these modes is also provided so as to determine the distance from a single transducer to the source of said lamb waves.

2 Claims, 3 Drawing Sheets

IDENTIFYING SOURCE OF ACOUSTIC EMISSIONS IN STRUCTURES USING LAMB WAVES AND VIBRATION MODES

FIELD OF THE INVENTION

The present invention relates to nondestructive evaluation techniques, particularly to source location of acoustic emission events and more particularly to the use of source location of acoustic emissions for structural monitoring.

BACKGROUND OF THE INVENTION

Acoustic emissions are small sound waves caused by microseismic activity within any material. In steel bridges, such acoustic emissions are caused by fatigue crack growth, friction of crack surfaces, rubbing at connections, noise directly generated by traffic, and the like. The monitoring of these microseismic waves can be accomplished by one or more piezoelectric transducers which convert the mechanical waves to electrical signals. The detection, amplification, counting, filtering and analyzing of these signals constitute the present state of the art in acoustic emission technology. Subsequent data analysis generally falls into two categories including: (i) analysis for acoustic event rate, event count, and frequency characteristics; and, (ii) analysis for location of the source of the acoustic emission event based on the time of arrival of the same acoustic emission event at a number of different transducers.

Structural monitoring for containment structures, e.g., pressure vessels, has been a driving force behind development of much of the acoustic emission instrumentation currently available. Materials Evaluation, "Acoustic Emission Testing" Feb. 1988, presents a general review of developments in industrial applications of monitoring techniques. Bridge monitoring is generally discussed by Gong et al., "Acoustic Emission Monitoring of Steel Railroad Bridges", Materials Evaluation, July 1992, pp. 883–887, and by Carlyle et al., in 1993 reports to the U.S. Department of Transportation regarding acoustic emission monitoring of the I-205 Willamette River bridge and the I-10 Mississippi River bridge. Proper techniques for the inspection of a structure such as a bridge superstructure are important in making rational decisions regarding rehabilitation, repair or replacement. With the increased public awareness of the decaying national infrastructure, the search for improved nondestructive evaluation techniques is magnified. Despite all the work in the area of nondestructive evaluation techniques, present techniques suffer from deficiencies including, e.g., a certain level of subjectiveness.

It is an object of the present invention to provide a process of determining a rough or approximate location of an acoustic emission event using a single transducer.

Another object of the invention is to provide a process of determining the source location of an acoustic emission event using the vibration modes of the structure together with the generated Lamb waves.

Still another object of the present invention is to provide a process for acoustic emission event monitoring with reduced subjective nature.

SUMMARY OF THE INVENTION

To achieve the foregoing and other objects, and in accordance with the purposes of the present invention, as embodied and broadly described herein, the present invention provides a process for global monitoring of a structure for location of a source of acoustic emissions including determining the vibration modes of a structure, measuring repetition rate of acoustic emission events in said structure, and, determining source location of said acoustic emission events in said structure. The present invention further provides a process for determining distance from an acoustic emission source on a structure to a transducer including determining the arrival times at a single receiving transducer of at least two different lamb wave modes generated by an acoustic emission source on a structure, and, calculating the distance from the transducer to the acoustic emission source by use of known velocities of said different lamb wave modes through said structure in combination with said determined arrival times. Still further, the present invention provides an apparatus for determination of source location of acoustic emissions in a structure including a single transducer for receiving signals from acoustic emissions of said structure, said transducer capable of receiving Lamb wave signals, a filtering means for separating different Lamb wave modes from said received signals, and a means for calculating said source location of acoustic emissions in said structure from said received signals and known Lamb wave mode velocities in said structure.

DETAILED DESCRIPTION

The present invention is concerned with a global monitoring process and apparatus for locating the source of acoustic emissions in structures such as bridges by use of generated Lamb waves and vibration modes of the particular structure. This invention deals with the detection of the source of sound waves. The process of the present invention relies not on the maximum amplitude or on the time rise but rather on the arrival of Lamb waves of certain frequency. The specific group and phase velocities of that frequency is used in determining the acoustic emission source. The emphasis of the present invention is in using the velocities of known frequency components in various source location schemes as opposed to determining the frequency content of the acoustic emission waves.

The dominant mode of wave propagation in, e.g., steel plates, is referred to as "Lamb waves" and is shown in FIG. 2. Lamb waves propagate great distances with very little attenuation. Additionally, propagation of Lamb waves is dependent upon the frequency of the sound wave, i.e., acoustic emission, and the consequent propagation mode. As the wave propagates, the different frequencies disperse and propagate at different velocities. Various phase velocities (Cp) and group velocities (Cg) are related through the wave number k by the equation:

$$Cg = Cp + k[\delta Cp/\delta k].$$

The Lamb wave propagation modes can be used to implement two different source location schemes. First, using transducers with a specific resonant frequency, the propagation phase velocity of the fastest mode that will propagate in that plate can first be determined. This velocity, rather than the P-wave velocity, is used in conventional source-location algorithms to give more accurate source location. Second, using only a single transducer that can detect two or more modes of Lamb waves, arrival of two different modes at the transducer can be detected. Since the velocities of each of these modes are different, they will arrive at the transducer at different times. Based on this time difference, a linear source-location can be done, which for three dimensional (3-D) structural components, can reveal the approximate location of the acoustic emission source.

Figure 1:
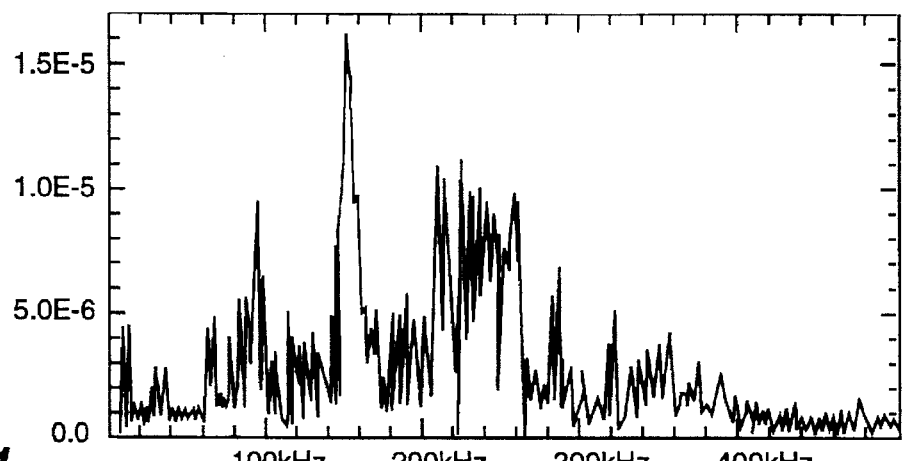
FIG. 1 shows a typical frequency content of acoustic emission events from tests in accordance with the present invention.
Figure 2A:
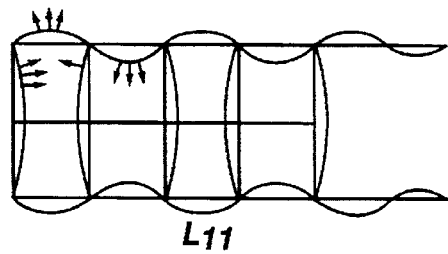
FIGS. 2(a)–2(d) show the dominant modes of wave propagation in a steel plate.
Figure 2B:
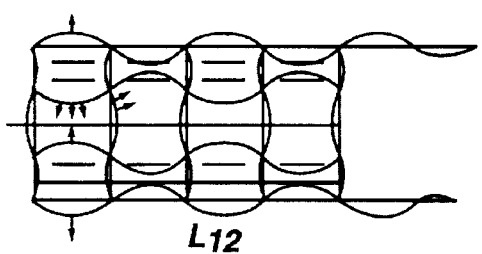
Figure 2C:
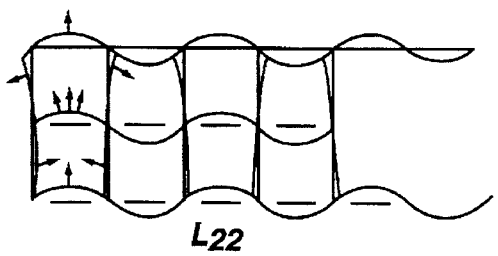
Figure 2D:
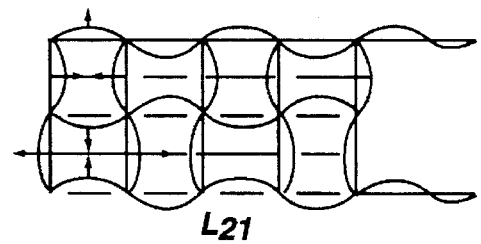
Figure 3:
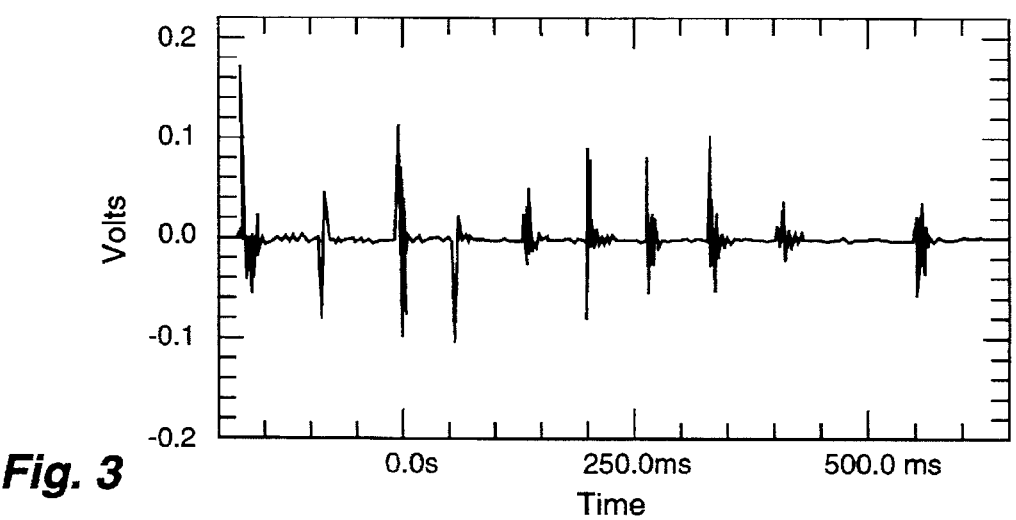
FIG. 3 shows the repetition pattern of an acoustic emission event on a structural article in accordance with the present invention.

During field testing of a bridge, it was found that the acoustic emission events had regular repetitions as shown in FIG. 3. Subsequently, it was determined that multiple acoustic emission events correspond exactly to the resonance of an individual member responsible for the particular acoustic emission event. Therefore, as part of the process of the present invention, the frequency response of an individual structural component, e.g., a bridge component, is first recorded. Then, the acoustic emission repetitions can be used for determining the source of the acoustic emission event.

By looking at the separation in time (due to dispersion) of the different frequencies in the same acoustic emission event, location of the source of the acoustic emission event can be accomplished with a single transducer. For example, it was possible to observe progressively larger separation of the 100 kHz, 160 kHz, and 240 kHz modes, as an acoustic emission event was monitored further in distance from its source. The time interval between the arrival of any two frequencies can be determined by various techniques. For instance, different frequencies can be separated by digital (or analog) filtering and the arrival time of each specific frequency separately determined. Another way is to cross-correlate the acoustic emission waveform with a synthetic waveform with the required frequency, which will reveal the onset or arrival of that particular frequency in the acoustic emission wave. Since the velocities of the two frequencies are known, the distance of the acoustic emission event can then be determined from the separation time. While this distance may give only a rough or approximate location of the source of acoustic emissions, the ability to have an approximate location then allows for a more detailed and localized evaluation in a particular region of a large structure such as a bridge thereby saving both time and expense.

Figure 8:
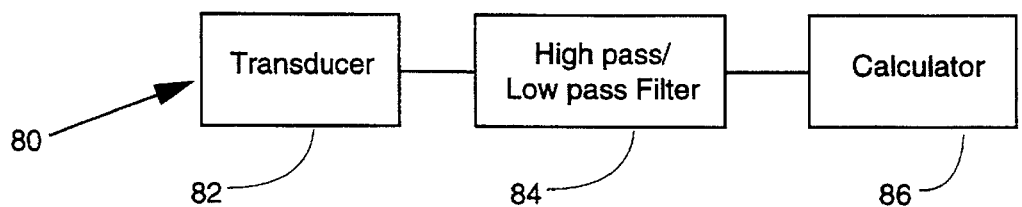
FIG. 8 shows a block drawing of the apparatus of the present invention for determination of source location of acoustic emissions in a structure.

In one embodiment of the present invention, transducers, e.g., accelerometers, can be mounted on different members of structure such as a bridge to determine the natural frequencies and mode shapes of the individual members. These natural frequencies and mode shapes are used to subsequently interpret particular acoustic emission events from the particular structure. Repetitions of acoustic emission events are related to the dynamics of the particular member which is the source of acoustic emission events. The interval between subsequent acoustic emission events is used to determine approximate source of the acoustic emissions. Repetition time is matched with the known (previously measured) natural frequencies of the bridge members to identify possible locations of the acoustic emission source. FIG. 8 shows a block drawing of apparatus 80 used in determining the source location of acoustic emissions in a structure and includes transducer 82, high and low pass filter 84 and a calculator 86 as a means for calculating the source location.

The present invention is more particularly described in the following example which is intended as illustrative only, since numerous modifications and variations will be apparent to those skilled in the art.

EXAMPLE

Figure 4:
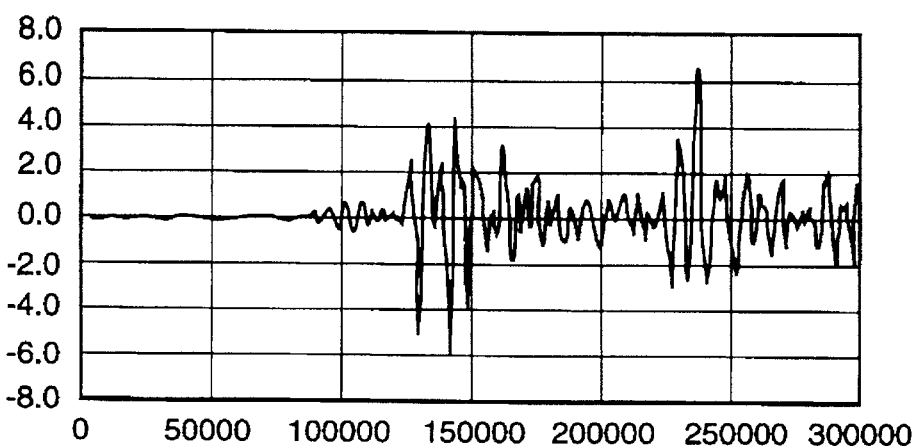
FIG. 4 shows an output from a transducer on an acoustic emission event located at a selected distance from the transducer.
Figure 5:
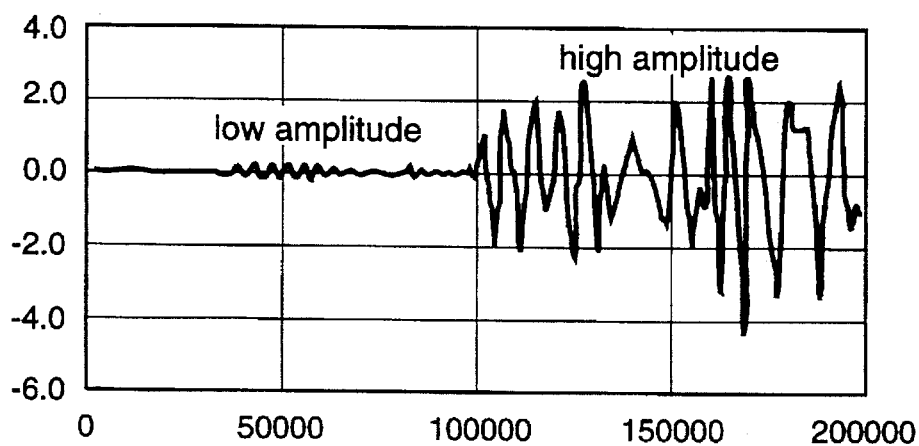
FIG. 5 shows an output from a transducer on an acoustic emission event located at twice the selected distance from the transducer as in FIG. 4.
Figure 6:
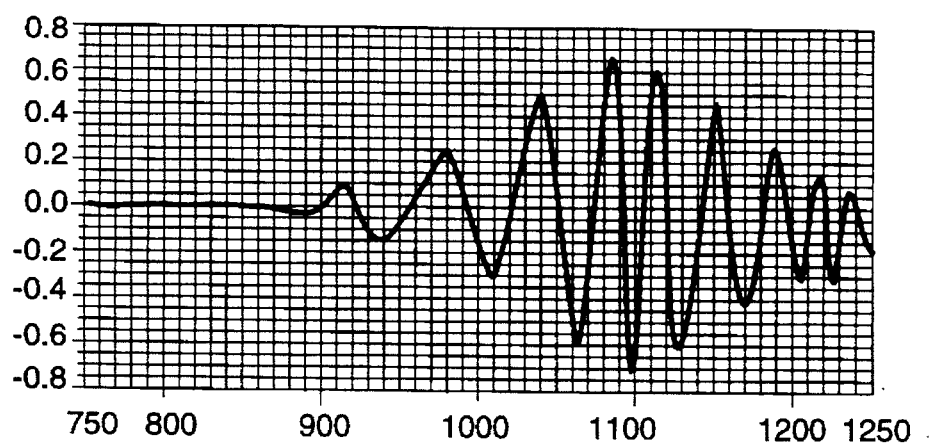
FIG. 6 shows the data from FIG. 4 after filtering by a high-pass filter.
Figure 7:
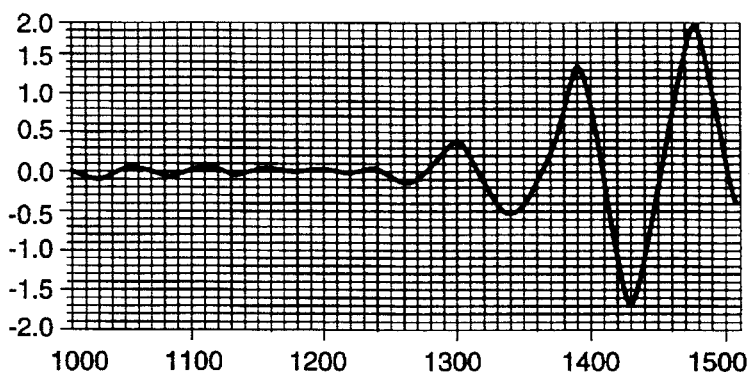
FIG. 7 shows the data from FIG. 4 after filtering by a low-pass filter.

FIG. 4 shows an acoustic emission event 30.5 cm (12") from the transducer in the time domain. This event had dominant frequencies between 100–150 and 200–250 kHz. The time scale is in nanoseconds. FIG. 5 shows similar data for an acoustic emission event 61 cm (24") away. Note the arrival of a low amplitude wave prior to a high amplitude wave in both FIG. 4 and FIG. 5. The low amplitude wave shown in FIG. 5 is twice as long as the data in FIG. 4. The data in FIG. 4 was subsequently filtered using a digital finite impulse response (FIR) filter. FIG. 6 shows the effect of high-pass filtering (x-axis shows the data points, 100 nanoseconds apart). The initial low amplitude signal was predominantly of higher frequency (above 190 kHz) and arrived at about 900. A low-pass filtering (lower than 110 kHz) of the same signal showed (FIG. 7) that the amplitude was practically zero prior to about 1250. Hence, the frequency component lower than 110 kHz arrives about 35000 nanoseconds later. This result was also verified for the signal in FIG. 5, and for other signals 15.2 cm (6") away.

This observation was consistent with the fact, verified from the experiments, that a symmetric lamb wave $L_{11}$ propagated with a velocity close to 5400 meters per second (m/s), while an asymmetric lamb wave $L_{21}$ travels much slower, with a velocity approximately equal to 3300 m/s. The 35000 nanosecond separation of the two modes after 30.5 cm is explained by this difference in velocities. When an acoustic emission event occurs further away from the transducer, the two modes are further separated as in FIG. 5. The source to transducer distance can therefore be determined from the separation of the two modes at a single transducer.

Although the present invention has been described with reference to specific details, it is not intended that such details should be regarded as limitations upon the scope of the invention, except as and to the extent that they are included in the accompanying claims.

What is claimed is:

1. An apparatus for determination of source location of acoustic emissions in a structure comprising:

a single transducer for receiving signals from acoustic emissions of said structure, said transducer receiving Lamb wave signals;

a filtering means for separating different Lamb wave modes from said received signals;

a means for calculating said source location of acoustic emissions in said structure from said received signals and known Lamb wave mode velocities in said structure.

2. The apparatus of claim 1 wherein said filtering means for separating different Lamb wave modes includes a high-pass filter and a low-pass filter.

* * * * *